United States Patent [19]

Grigg et al.

[11] Patent Number: 5,221,627
[45] Date of Patent: Jun. 22, 1993

[54] FINGERPRINT REAGENT

[75] Inventors: Ronald E. Grigg, Leeds; Charles A. Pounds, Reading, both of United Kingdom; Teirevat Mongkolaussavaratana, Bangkok, Thailand

[73] Assignee: The Queen's University of Belfast, Northern Ireland, Northern Ireland

[21] Appl. No.: 689,750

[22] PCT Filed: Nov. 9, 1989

[86] PCT No.: PCT/GB89/01329

§ 371 Date: May 24, 1991

§ 102(e) Date: May 24, 1991

[87] PCT Pub. No.: WO90/05308

PCT Pub. Date: May 17, 1990

[30] Foreign Application Priority Data

Nov. 9, 1988 [GB] United Kingdom ............... 8826237

[51] Int. Cl.$^5$ ............................................ G01N 33/68
[52] U.S. Cl. ..................................... 436/89; 436/112; 436/113; 436/164; 436/172
[58] Field of Search .................. 436/89, 90, 172, 147, 436/8, 111, 172, 164

[56] References Cited

PUBLICATIONS

Wittman, H. et al. "New reagents for the detection of amino acids by paper chromatography," Monatsh. Chem., 101(5), 1388-1393, 1970.

Primary Examiner—James C. Housel
Assistant Examiner—David Redding
Attorney, Agent, or Firm—Thomas W. Tolpin

[57] ABSTRACT

A method of detection of amino acids comprising the application, to the material being tested, of a reagent comprising the following basic formula:

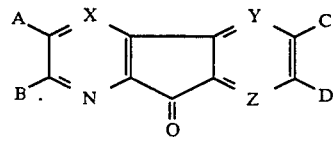

where X, Y and/or Z may be nitrogen C—H, C-alkyl or C-aryl and wherein A, B, C and/or D may be an alkyl or aryl substituent either alone or in combination.

12 Claims, No Drawings

FINGERPRINT REAGENT

This invention relates to a method for the detection and or quantitation of α-amino acids in chemical and biochemical analyses and particularly but not exclusively to a method for the detection of latent fingerprints.

At present a common method of detection of amino acids comprises applying ninhydrin (1,2,3-triketohydrindene hydrate) to the amino acid. The ninhydrin reacts with the amino acid on heating yielding a purple colouration.

As amino acids are secreted from human finger tips, ninhydrin is often used in the detection of latent fingerprints, in, for example, criminal investigation.

We have discovered an alternative group of compounds which can be used for this purpose.

According to the present invention there is provided a method of detection of amino acids comprising the application, to the material being tested, of a reagent comprising the following basic formula:

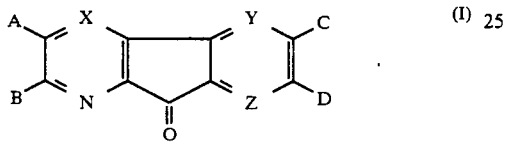

wherein X, Y and/or Z may be nitrogen, C—H, C-alkyl or C-aryl and wherein A, B, C and/or D may be an alkyl or aryl substituent either alone or in combination.

In a preferred embodiment of the invention the substituents X, Y, Z, A, B, C and D are one of the following combinations (1)
  X and Y are C—H
  Z is nitrogen
  A, B, C and D are hydrogen
(2)
  X is nitrogen
  Y and Z are C—H
  A and B together are part of a benzene ring
  C and D are hydrogen
(3)
  X, Y and Z are nitrogen
  A, B, C and D are hydrogen
(4)
  X, Y and Z are nitrogen
  A and B together are part of a benzene ring
  C and D together are part of a benzene ring
(5)
  X and Y are C—H
  Z is nitrogen
  A and B together are part of a benzene ring
  C and D together are part of a benzene ring
(6)
  Z is nitrogen
  B and D are hydrogen
  A and X together form part of a benzene ring
  C and Y together form part of a benzene ring
(7)
  X and Z are nitrogen
  Y is C—H
  A and B together form part of a benzene ring
  C and D are hydrogen.

In order that the invention may be more readily understood, a specific embodiment thereof will now be described by way of example:

A method of detecting amino acids comprises the addition to the material being tested of a compound comprising the following basic structure

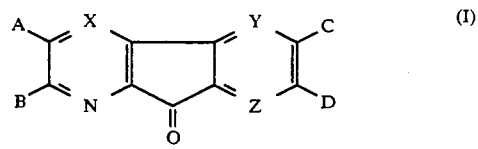

wherein X, Y and Z may be nitrogen, C—H, C-alkyl or C-aryl and A, B, C and D may be alkyl, aryl alkyl or aryl substituent either alone or in combination.

Some preferred examples of the compound used in the method are as follows:

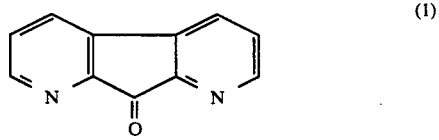

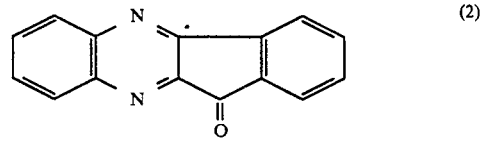

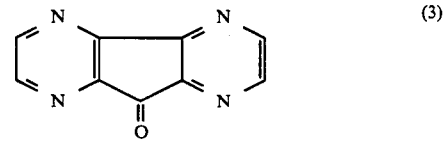

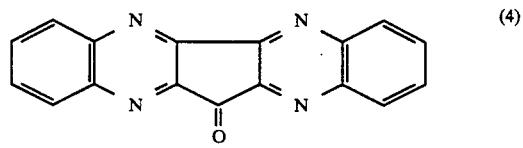

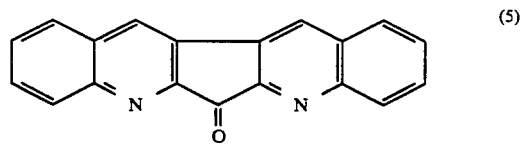

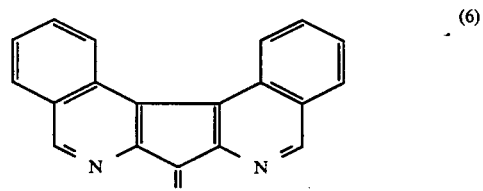

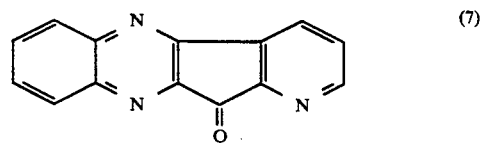

Many substituents of functional groups are possible. Each ring could be variously substituted, for example, with alkyl and aryl substituents.

The compounds of the method of the invention may be synthesized by a variety of methods. One such method of producing such a compound is disclosed in Helv.Chim.Acta., 1950, 50, 1080, which reveals a method of synthesising 1,8-Diazafluoren-9-one (1). Other compounds of the invention could be produced, for example, by appropriate substitution reactions of 1,8-Diazofluoren-9-one of (1).

In practice the compound (I) is dissolved in a suitable solvent system such as methanol/acetic acid/trichlorotrifluorethane so as the concentration of the reagent (I) solution is in the range from substantially 0.05 to 2%.

The document or sample containing or supporting the amino acid such as a latent fingerprint is immersed in the reagent (I) solution. The amino acid sample may be subsequently be removed from the reagent (I) solution after a suitable time period has elapsed, for example approximately five seconds. The sample is then allowed to dry. Drying should be complete after approximately thirty seconds. The sample is then re-immersed in the reagent (I) solution for example for thirty seconds. The sample is subsequently removed from the reagent (I) solution and the amino acids may then be developed by, for example, heating the sample at 110° C. for ten minutes.

The reagent (I) in combination with the amino acid produces coloured fluorescent species with λ (excitation) in the order of 470 nm and λ (emission) in the order of 570 nm on paper. The fluorescent fingerprints can be made visible by using blue/green light for excitation and observing the light emission through a filter such as a 610 nm filter.

The invention will now be further illustrated by the following examples.

EXAMPLE 1

1,8-Diazafluoren-9-one (1) (0.05 g) was dissolved in a mixture of methanol (4 ml) and acetic acid (2 ml) and was then diluted up to 100 ml with trichlorotrifluoroethane (Fluorosil) so as to form a reagent (1) solution. A sheet of paper on which a latent fingerprint was situated, was immersed in the reagent (1) solution for 5 seconds. The paper was removed from the reagent (1) solution and allowed to dry for 30 seconds. The paper was then immersed for a further five seconds and was subsequently removed from the reagent (1) solution and heated at 110° C. for 10 minutes.

The fluorescent fingerprints were made visible by illumination with blue/green light (excitation) and were observed through a 610 nm filter.

The fluorescent fingerprints visualised by reagent (1) proved to reveal more fingerprint detail than ninhydrin.

EXAMPLE 2

The method of Example 1 was repeated substituting reagent (1) for reagents (2) to (7). Reagents (2) to (7) also produced fluorescent fingerprints which could be visualised by illumination with blue/green light (excitation) and observed through a 610 nm filter.

It is to be understood that the scope of the invention should not be limited to the above described embodiments thereof as those embodiments are for illustration only.

We claim:

1. A method of detection of amino acids comprising the application, to the material being tested, of a reagent comprising the following basic formula;

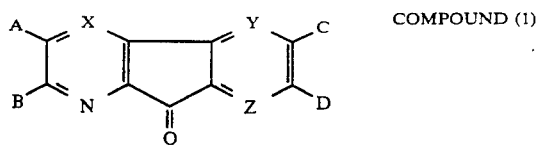

COMPOUND (1)

wherein X, Y and Z is nitrogen, C—H, C-alkyl or C-aryl and wherein A, B, C and D is an alkyl or aryl substituent either alone or in combination, said material being tested comprising amino acids, and detecting said amino acids by reacting said amino acids with said reagents to provide a visual change in the material being tested.

2. A method of detection of amino acids as claimed in claim 1, wherein substituents X, Y, Z, A, B, C, and D are one of the following combinations
   (a) X and Y are C—H; and
   Z is nitrogen; and
   A, B, C and D are hydrogen
   (b) X is nitrogen; and
   Y and Z are C—H; and
   A and B together are part of a benzene ring; and
   C and D are hydrogen or
   (c) X, Y and Z are nitrogen; and
   A, B, C and D are hydrogen or
   (d) X, Y and Z are nitrogen; and
   A and B together are part of a benzene ring; and
   C and D together are part of a benzene ring or
   (e) X and Y are C—H; and
   Z is nitrogen; and
   A and B together are part of a benzene ring; and
   C and D together are part of a benzene ring or
   (f) Z is nitrogen; and
   B and D are hydrogen; and
   A and X together form part of a benzene ring; and
   C and Y together form part of a benzene ring or
   (g) X and Z are nitrogen;
   Y is C—H;
   A and B together form part of a benzene ring;
   C and D are hydrogen.

3. A method of detection of amino acids as claimed in claim 1, wherein the said compound (1) is dissolved in a solvent system comprising at least one of the following: alcohol, acid or halo alkane to form a solution.

4. A method of detection of amino acids as claimed in claim 1, wherein the said compound (1) is dissolved in a solvent system comprising methanol, acetic acid and trichlorotrifluoroethane to form a solution.

5. A method of detection of amino acids as claimed in claim 3 wherein the material being tested is immersed in the compound (1) solution.

6. A method of detection of amino acids as claimed in claim 1 in which the material being tested is substantially dried after a first application of compound (1) prior to a second application of compound (1) to the material being tested.

7. A method of detection of amino acids as claimed in claim 1 in which the visual change is developed by heating.

8. A method of detection of amino acids comprising the application, to the material being tested, of a reagent comprising the following basic formula;

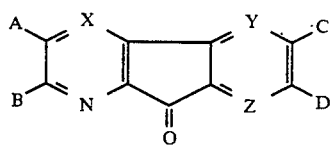

COMPOUND (1)

wherein X, Y and Z is nitrogen, C—H, C-alkyl or C-aryl and wherein A, B, C and D is an alkyl or aryl substituent either alone or in combination, in which the amino acid in combination with compound (1) produces coloured fluorescent species which is made visible by illumination by light with a certain wavelength range.

9. A method of detection of amino acids as claimed in claim 8 in which the excitation wavelength range comprises 470 nm and the emission wavelength range comprises 570 nm.

10. A method of detection of amino acids as claimed in claim 2, wherein the said compound (1) is dissolved in a solvent system comprising at least one of the following: alcohol, acid or halo alkane.

11. A method of detection of amino acids as claimed in claim 2, wherein the said compound (1) is dissolved in a solvent system comprising methanol, acetic acid and trichlorotrifluorethane.

12. A method of detection of amino acids as claimed in claim 4, wherein the material being tested is immersed in the compound (1) solution.

* * * * *